(12) United States Patent
Bawendi et al.

(10) Patent No.: US 8,481,162 B2
(45) Date of Patent: Jul. 9, 2013

(54) STABILIZED SEMICONDUCTOR NANOCRYSTALS COMPRISING A COATING OF POLYDENTATE LIGAND

(75) Inventors: Moungi G. Bawendi, Boston, MA (US); Sungjee Kim, Cambridge, MA (US); Nathan E. Stott, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 20 days.

(21) Appl. No.: 12/585,303

(22) Filed: Sep. 10, 2009

(65) Prior Publication Data

US 2010/0102277 A1 Apr. 29, 2010

Related U.S. Application Data

(63) Continuation of application No. 11/543,829, filed on Oct. 6, 2006, now Pat. No. 7,601,424, which is a continuation of application No. 10/641,292, filed on Aug. 15, 2003, now Pat. No. 7,160,613.

(60) Provisional application No. 60/403,367, filed on Aug. 15, 2002.

(51) Int. Cl.
- *B32B 5/16* (2006.01)
- *B05D 7/00* (2006.01)

(52) U.S. Cl.
USPC .......... 428/403; 427/215; 427/216; 427/220; 427/402; 977/773; 977/777; 977/813; 977/827; 977/830

(58) Field of Classification Search
USPC .................. 428/403; 977/773, 777, 813, 827, 977/830; 427/215, 216, 220, 402
See application file for complete search history.

(56) References Cited

U.S. PATENT DOCUMENTS

| | | | |
|---|---|---|---|
| 5,262,357 A | 11/1993 | Alivisatos et al. |
| 5,505,928 A | 4/1996 | Alivisatos et al. |
| 5,525,377 A | 6/1996 | Gallagher et al. |
| 5,537,000 A | 7/1996 | Alivisatos et al. |
| 5,585,640 A | 12/1996 | Huston et al. |
| 5,674,698 A | 10/1997 | Zarling et al. |
| 5,677,545 A | 10/1997 | Shi et al. |
| 5,751,018 A | 5/1998 | Alivisatos et al. |
| 5,985,173 A | 11/1999 | Gray et al. |
| 5,985,353 A | 11/1999 | Lawton et al. |
| 5,990,479 A | 11/1999 | Weiss et al. |
| 6,054,495 A | 4/2000 | Markowitz et al. |
| 6,103,868 A | 8/2000 | Heath et al. |
| 6,114,038 A | 9/2000 | Castro et al. |

(Continued)

FOREIGN PATENT DOCUMENTS

| EP | 0 800 852 A2 | 10/1997 |
|---|---|---|
| WO | WO 97/10175 | 3/1997 |

(Continued)

OTHER PUBLICATIONS

Alivisatos et al., "Organization of 'nanocrystal molecules' using DNA," *Nature*, 382:609-611, Aug. 15, 1996.

(Continued)

*Primary Examiner* — Hoa (Holly) Le
(74) *Attorney, Agent, or Firm* — Steptoe & Johnson LLP (57) ABSTRACT

A semiconductor nanocrystal associated with a polydentate ligand. The polydentate ligand stabilizes the nanocrystal.

21 Claims, 3 Drawing Sheets

Chemical structures of oligomeric phosphine families (n = 1, 2, 3, or 4);

Oligomeric phosphine R=H

Oligomeric phosphine with octyl alkyl chain R=

Oligomeric phosphine with hexadecyl alkyl chain R=

Oligomeric phosphine with methacrylate R=

Oligomeric phosphine with carboxylic acid R=

U.S. PATENT DOCUMENTS

| | | | |
|---|---|---|---|
| 6,139,585 A | 10/2000 | Li | |
| 6,207,229 B1 | 3/2001 | Bawendi et al. | |
| 6,214,729 B1* | 4/2001 | Uhlenbrock et al. | 438/681 |
| 6,251,303 B1 | 6/2001 | Bawendi et al. | |
| 6,294,401 B1 | 9/2001 | Jacobson et al. | |
| 6,306,610 B1 | 10/2001 | Bawendi et al. | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,337,117 B1 | 1/2002 | Maenosono et al. | |
| 6,379,635 B2 | 4/2002 | O'Brien et al. | |
| 6,444,143 B2 | 9/2002 | Bawendi et al. | |
| 6,447,698 B1 | 9/2002 | Ihara et al. | |
| 6,501,091 B1 | 12/2002 | Bawendi et al. | |
| 6,548,168 B1 | 4/2003 | Mulvaney et al. | |
| 6,548,171 B1 | 4/2003 | Barbera-Guillem et al. | |
| 6,576,291 B2 | 6/2003 | Bawendi et al. | |
| 6,602,671 B1 | 8/2003 | Bawendi et al. | |
| 6,607,829 B1 | 8/2003 | Bawendi et al. | |
| 6,797,412 B1 | 9/2004 | Jain et al. | |
| 6,846,565 B2 | 1/2005 | Korgel et al. | |
| 6,858,158 B2 | 2/2005 | Chittibabu et al. | |
| 6,864,626 B1 | 3/2005 | Weiss et al. | |
| 6,921,496 B2* | 7/2005 | Anderson et al. | 252/301.6 S |
| 7,160,613 B2* | 1/2007 | Bawendi et al. | 428/403 |
| 7,205,048 B2 | 4/2007 | Naasani | |
| 7,488,819 B2* | 2/2009 | Manabe et al. | 540/472 |
| 7,601,424 B2* | 10/2009 | Bawendi et al. | 428/403 |
| 7,662,313 B2* | 2/2010 | Whiteford et al. | 252/500 |
| 7,862,892 B2* | 1/2011 | Chan et al. | 428/403 |
| 2001/0005495 A1 | 6/2001 | O'Brien et al. | |
| 2002/0066401 A1 | 6/2002 | Peng et al. | |
| 2003/0017264 A1 | 1/2003 | Treadway et al. | |
| 2003/0042850 A1 | 3/2003 | Bertram et al. | |
| 2004/0091710 A1* | 5/2004 | Bawendi et al. | 428/407 |
| 2004/0265622 A1 | 12/2004 | Sadasivan et al. | |
| 2005/0112376 A1 | 5/2005 | Naasani | |

FOREIGN PATENT DOCUMENTS

| | | |
|---|---|---|
| WO | WO 98/04740 | 2/1998 |
| WO | WO 98/33070 | 7/1998 |
| WO | WO 99/26299 | 5/1999 |
| WO | WO 00/27365 | 5/2000 |
| WO | WO 00/27436 | 5/2000 |
| WO | WO 00/28088 | 5/2000 |
| WO | WO 00/28089 | 5/2000 |
| WO | WO 2005/004253 | 1/2005 |
| WO | WO 2005/017951 | 2/2005 |

OTHER PUBLICATIONS

Alivisatos et al., "Semiconductor Clusters, Nanocrystals, and Quantum Dots," *Science*, 271:933-937, 1996.

Alivisatos, "Perspectives on the Physical Chemistry of Semiconductor Nanocrystals" *J. Phys. Chem.* 1996(100):13226-13239, 1996.

Bawendi et al., "Luminescence properties of CdSe quantum crystallites: resonance between interior and surface localized states," *J. Chem. Phys.*, 96(2):946-954, Jan. 15, 1992.

Beverloo et al., "Preparation and Microscopic Visualization of Multicolor Luminescent Immunophosphors," *Cytometry*, 13:561-570, 1992.

Bruchez et al., "Semiconductor Nanocrystals as Fluorescent Biological Labels," *Science*, 281:2013-2016, Sep. 25, 1998.

Chan et al., "Quantum Dot Bioconjugates for Ultrasensitive Nonisotopic Detection," *Science*, 281:2016-2018, 1998.

Coffer et al., "Characterization of quantum-confined CdS nanocrystallites stabilized by deoxyribonucleic acid (Dna)," *Nanotechnology*, 3:69-76, 1992.

Correa-Duarte et al., "Stabilization of CdS semiconductor nanoparticles against photodegradation by silica coating procedure," *Chem. Phys. Lett.*, 286:497-501, Apr. 17, 1998.

Dabbousi, et al., "(CdSe)ZnS core-shell quantum dots: synthesis and characterization of a size series of highly luminescent nanocrystallites" *J. of Phys. Chem. B* 101(46):9463-9475, Nov. 13, 1997.

Danek et al., "Synthesis of Luminescent Thin-Film CdSe/ZnSe Quantum Dot Composites Using CdSe Quantum Dots Passivated with an Overlayer of ZnSe" *Chem. Mater.* 8(1):173-180, 1996.

Gan et al., "Enhanced Photoluminescence and Characterization of Mn-Doped ZnS Nanocrystallites Synthesized in Microemulsion" *Langmuir* 1997(13):6427-6431, 1997.

Gao et al., "Strongly Photoluminescent CdTe Nanocrystals by Proper Surface Modification," *J. Phys. Chem.*, 102:8360-8363, 1998.

Hines et al., "Synthesis and Characterization of Strongly Luminescing ZnS-Capped CdSe Nanocrystals" *J. Phys. Chem.* 100:468-471, Jan. 1996.

Jarvis et al., "Solution Synthesis and Photoluminescence Studies of Small Crystallites of Cadmium Telluride," *Mat. Res. Soc. Symp. Proc.*, 272:229-234, 1992.

Kortan et al., "Nucleation and Growth of CdSe on ZnS Quantum Crystallite Seeds, and Vice Versa, in Inverse Micelle Media" *J. Am Chem. Soc.* 112:1327-1332, 1990.

Kuno et al., "The band edge luminescence of surface modified CdSe nanocrystallites: Probing the luminescing state" *J. Chem. Phys.* 106(23):9869-9882, Jun. 1997.

Lawless et al., "Bifunctional Capping of CdS Nanoparticles and Bridging to TiO2" *J. Phys. Chem.* 99:10329-10335, 1995.

Lee et al., "Surface Derivatization of Nanocrystalline CdSe Semiconductors," *Mat. Res. Soc. Symp. Proc.*, 452:323-328, 1997.

Lee, J. et al., "Full Color Emission from II-VI Semiconductor Quantum Dot-Polymer Composites," *Adv. Mater.* 12:1102-1105, 2000.

Liz-Marzan et al., "Synthesis of Nanosized Gold-Silica Core-Shell Particles" *Langmuir* 12:4329-4335, 1996.

Ludolph, B., et al., "Novel single molecule precursor routes for the direct synthesis of highly monodispersed quantum dots of cadmium or zinc sulfide or selenide," *Chem. Commun.* 1998: 1849-1850, 1998.

Mahtab et al., "Preferential-absorption of a 'kinked' DNA to a newtral curved surface: comparison to and implications for nonspecific DNA-protein interactions," *J. Am. Chem. Soc.*, 118:7028-7032, Jul. 31, 1996.

Mahtab et al., "Protein-sized quantum dot luminescence can distinguish between 'straight', 'bent', and 'kinked' oligonucletides", *J. Am. Chem. Soc.*, 117:9099-9100, Sep. 6, 1995.

Matsumoto et al., "Preparation of Monodisperse CdS Nanocrystals by Size Selective Photocorrosion" *J. Phys. Chem.*100(32):13781-13785, 1996.

Mattoussi, H., et al. "Self-assembly of CdSe-ZnS Quantum Dot Bioconjugates Using an Engineered Recombinant Protein," *J. Am. Chem. Soc.* 122:12142-12150, 2000.

Mikulec et al., "Fluorescent semiconductor nanocrystallites derivatized with biomolecules" *Amer. Chem.. Soc. Nat'l Meeting*, Boston, MA, Aug. 24, 1998.

Murphy et al., "Quantum dots as inorganic DNA-binding proteins," *Mat. Res. Soc. Symp.*, 452:597-600, 1997.

Murray et al., "Synthesis and Characterization of Nearly Monodisperse CdE (E=S, Se, Te) Semiconductor Nanocrystallites" *J. Am. Chem. Soc.* 115(19):8706-8715, 1993.

Nirmal et al., "Fluorescence Intermittency in single Cadmium Selenide Nanocrystals" *Nature* 383:802-804, Oct. 1996.

Pehnt et al., "Nanoparticle Precursor Route to Low-Temperature Spray Deposition of CdTe Thin Films," *Appl. Phys. Lett.*, 67(15):2176-2178, Oct. 9, 1995.

Peng et al., "Epitaxial Growth of Highly Luminescent CdSe/CdS Core/Shell Nanocrystals with Photostability and Electronic Accessibility," *J. Am. Chem. Soc.*, 119:7019-7029, Jul. 30, 1997.

Peng et al., "Synthesis and Isolation of a Homodimer of Cadmium Selenide Nanocrystals," *Angewandte Chemie*, 36:145-147, Feb. 3, 1997.

Rajh et al., "Synthesis and Characterization of Surface-Modified Colloidal CdTe Quantum Dots" *J. Phys. Chem.* 97:11999-12003, Nov. 1993.

Rogach et al., "Synthesis and characterization of Thiol-Stabilized CdTe Nanocrystals" *Ber. Bunsenges. Phys. Chem.* 100(11):1772-2778, 1996.

Spanhel et al., "Photochemistry of Colloidal Semiconductors. Surface Modification and Stability of Strong Luminescing CdS Particles" *J. Am. Chem. Soc.*109(19):5649-5655, 1987.

Steigerwald et al., "Surface Derivatization and Isolation of Semiconductor Cluster Molecules," *J. Am. Chem. Soc.*, 110:3046-3050, 1988.

Whitesell, "Directionally Aligned Helical Peptides on Surfaces", *Science*, 261:73-75, Jul. 2, 1993.

Bhargava, R.N., et al., "Quantum Confined Atoms of Doped ZnO Nanocrystals", *Phys. Stat. Sol* (b) 229, No. 2, 897-901 (2002).

Sirenko, A.A., et al., "Spin-flip and acoustic-phonon Raman scattering in CdS nanocrystals", *Physical Review B*, vol. 58, No. 4, 15 (Jul. 1998-II), 2077-2087.

Lublinskaya, O., et al., "CdS nanocrystal growth in thin silica films: evolution of size distribution function", *Journal of Crystal Growth* 184/185 (1998) 360-364.

Valenta, J., et al., "Dynamics of excitons in CuBr nanocrystals: Spectral-hole burning and transient four-wave-mixing measurements," *Physical Review B*, vol. 57, No. 3, Jan. 15, 1998-I, 1774-1783.

Saviot, L., et al., "Size-selective resonant Raman scattering in CdS doped glasses," *Physical Review B*, vol. 57, No. 1, Jan. 1, 1998-I, 341-346.

Ekimov, A.I., "Growth and optical properties of semiconductor nanocrystals in a glass matrix," *Journal of Luminescence* 70 (1996) 1-20.

Saviot, L., et al., "Size dependence of acoustic and optical vibrational modes of CdSe nanocrystals in glasses," *Journal of Non-Crystalline Solids* 197 (1996) 238-246.

Itoh, T., et al., "Subpicosecond dynamics of confined excitons in CuCl nanocrystals," *Materials Science and Engineering* A217/218 (1996) 167-170.

Chamarro, M., et al., "Enhancement of electron-hole exchange interaction in CdSe nanocrystals; A quantum confinement effect," *Physical Review B*, vol. 53, No. 3, Jan. 15, 1996-I, 1336-1342.

Edamatsu, K., et al., "Subpicosecond dynamics of confined excitons and optical nonlinearities of CuCl quantum dots," *Journal of Luminescence* 66 & 67 (1996) 406-409.

Chamarro, M., et al., "Size-dependent Electron-Hole Exchange Interaction in CdSe Quantum Dots, *Il Nuovo Cimento*," vol. 17, Nos. 11-12, (1995) 1407-1412.

Itoh, T., et al., "Polaron and Exciton-Phonon Complexes in CuCl Nanocrystals," *Physical Review Letters*, vol. 74, No. 9, Feb. 27, 1995, p. 1645-1648.

Ekimov, A., et al., "Growth of CdSe nanocrystals in ion-implanted $SiO_2$ films," *Journal of Crystal Growth* 151 (1995) 38-45.

Saviot, L., et al., "Effects of Resonance on Low-Frequency Raman Scattering From Semiconductor Nanocrystals," *Radiation Effects and Defects in Solids*, 1995, vol. 137, pp. 45-50.

Ekimov, A.I., "Optical Properties of Oxide Glasses Doped by Semiconductor Nanocrystals," *Radiation Effects and Defects in Solids*, 1995, vol. 134, pp. 11-22.

Chamarro, M., et al., "Enhancement of Exciton Exchange Interaction by Quantum Confinement in CdSe Nanocrystals," *Jpn. J. Appl. Phys*, vol. 34, 12-14 (1994).

Gurevich, S.A., et al., "Growth of CdS nanocrystals in silicate glasses and in thin $SiO_2$ films in the Initial states of the phase separation of a solid solution," *Semiconductors*, 28 (5), May 1994, 486-493.

Itoh, T. et al., "Interface effects on the properties of confined excitons in CuCl microcrystals," *Journal of Luminescence* 60 & 61 (1994) 396-399.

Jursenas, S., et al., "Surface Recombination of Nonequilibrium Electron-Hole Plasma in Laser-Modified Semiconductor-Doped Glasses," *Solid State Communications*, vol. 87, No. 6, 577-580 (1993).

Tamulaitis, G., et al., "Dynamics of Nonlinear Optical Response of CuBr-Doped Glasses," *Superlattices and Microstructures*, vol. 3, No. 2, 199-202 (1993).

Ekimov, A. I., et al., "Absorportion and intensity-dependent photoluminescence measurements on CdSe quantum dots: assignment of the first electronic transitions," *Journal of the Optical Society of America*, vol. 10, Nos. 1-12, 100-107 (1992).

Gurevich, S.A., et al. "Preparation and investigation of $SIO_2$ films activated by CdS semiconductor nanocrystals," *Soviet Physics Semiconductors*, vol. 26, 57-59 (1992).

Aktsipetrov, O.A., et al. "Generation of reflected second harmonic at semiconductor quantum dots," *JETP Letters*, vol. 55, No. 8, 435-439 (1992).

Ekimov, A.I., et al. "Dimensional Effects in Luminescence Spectra of Zero-Dimensional Semiconductor Structures," *Bulletin of the Russian Academy of Sciences*, vol. 56, No. 2, pp. 154-157, Feb. 1992.

Baltrameyunas, R., et al., "Fast switching of the transmission of light by glasses activated with CdS microcrystals," *Sov. Phys. Semicond.*, vol. 25 No. 2, 164-166 (1991).

Efros, A.L., et al., "Resonance Raman Spectroscopy of Electron-Hole Pairs—Polar Phonon Coupling in Semiconductor Quantum Microcrystals," *Solid State Communications*, vol. 78, No. 10, pp. 853-856, 1991.

Ekimov, A.I., et al., "Optics of Zero Dimensional Semiconductor Systems, *Acta Physica Polonica A*," vol. 79 (1991), No. 1. pp. 5-14.

Ekimov, A.I., "Optical Properties of Semiconductor Quantum Dots in Glass Matrix," *Physica Scripta*. vol. T39, 217-222 (1991).

Baltramiejunas, R., et al. "Rapid Processes of Darkening and Bleaching in CdS Doped Glasses," *Superlattices and Microstructures* vol. 10, No. 3, 307-310 (1990).

Chepic, D.I., et al., "Auger ionization of semiconductor quantum drops in a glass matrix," *Journal of Luminescence* 47 (1990) 113-127 North-Holland.

Dneproviskii, V.S., et al., "Time-Resolved Luminescence of CdSe Microcrystals," *Solid State Communications*, vol. 74, No. 7, pp. 555-557, 1990.

Ekimov, A.I., et al., "Quantum-Size Stark Effect in Semiconductor Microcrystals," *Journal of Luminescence* 46 (1990) 97-100 North-Holland.

Ekimov, A.I., et al., "Spectra and Decay Kinetics of Radiative Recombination in CdS Microcrystals," *Journal of Luminescence* 46 (1990) 83-95 North-Holland.

Ekimov, A.I., et al., "Influence of high hydrostatic pressures on the exciton spectrum of CdS microcrystals in glass," *Sov. Phys. Semicond.* 23(9), Sep. 1989, pp. 965-966.

Ekimov, A.I., et al., "Photoluminescence of quasizero-dimensional semiconductor structures," *Sov. Phys. Solid State* 31(8), Aug. 1989, pp. 1385-1393.

Grabovskis, V.Y., et al., "Photoionization of semiconducting microcrystals in glass," *Sov. Phys. Solid State* 31(1), Jan. 1989, pp. 149-151.

Ekimov, A.I., et al., "Donor-like Exciton in Zero-Dimension Semiconductor Structures," *Solid State Communications*, vol. 69, No. 5, pp. 565-568, 1989.

Ekimov, A.I., et al., "Nonlinear Optics of Semiconductor-Doped Glasses," *Phys. Stat. Sol.* (b) 150, (1988) pp. 627-633.

Vandyshev, Y.V., et al., "Nonlinear optical properties of semiconductor microcrystals," *JETP Lett.*, vol. 46, No. 10, Nov. 25, 1987 pp. 435-439.

Ekimov, A.I., et al., "Quantization of the energy spectrum of holes in the adiabatic potential of the electron," *JETP Lett.*, vol. 43, No. 6, Mar. 25, 1986, pp. 376-379.

Ekimov, A.I., et al., "Quantum Size Effect in Semiconductor Microcrystals," *Solid State Communications*, vol. 56, No. 11, pp. 921-924, 1985.

Ekimov, A.I., et al., "Size quantization of the electron energy spectrum in a microscopic semiconductor crystal," *JETP Lett.*, vol. 40, No. 8, Oct. 25, 1984, pp. 1136-1139.

Ekimov, A.I., et al., "Quantum size effect in the optical spectra of semiconductor microcrystals," *Sov. Phys. Semicond.* 16(7), Jul. 1982, pp. 775-778.

Ekimov, A.I., et al., "Quantum size effect in three-dimensional microscopic semiconductor crystals," *JETP Lett*, vol. 34, No. 6, Sep. 20, 1981, pp. 345-349.

Volkov, A.S., et al., "Oscillations of polarization of recombination radiation of a variable gap semiconductor in a magnetic field," *JETP Lett.*, vol. 25 No. 55, 526-528 (1977).

* cited by examiner

Chemical structures of oligomeric phosphine families (n = 1, 2, 3, or 4);

*Oligomeric phosphine* R=H

*Oligomeric phosphine with octyl alkyl chain* R=

*Oligomeric phosphine with hexadecyl alkyl chain* R=

*Oligomeric phosphine with methacrylate* R=

*Oligomeric phosphine with carboxylic acid* R=

STABILIZED SEMICONDUCTOR NANOCRYSTALS COMPRISING A COATING OF POLYDENTATE LIGAND

CLAIM OF PRIORITY

This application is a continuation of U.S. patent application Ser. No. 11/543,829, filed Oct. 6, 2006 now U.S. Pat. No. 7,601,424, which is a continuation of, and claims priority to, U.S. patent application Ser. No. 10/641,292, filed Aug. 15, 2003 now U.S. Pat. No. 7,160,613, and claims priority to provisional U.S. Patent Application Ser. No. 60/403,367, filed on Aug. 15, 2002, each of which is hereby incorporated by reference in its entirety.

FEDERALLY SPONSORED RESEARCH OR DEVELOPMENT

This invention was made with Government support under Grant No. N00014-01-1-0787, awarded by the US Navy. The Government has certain rights in this invention.

TECHNICAL FIELD

The invention relates to stabilized semiconductor nanocrystals.

BACKGROUND

Semiconductor nanocrystals have been a subject of great interest, promising extensive applications including display devices, information storage, biological tagging materials, photovoltaics, sensors and catalysts. Nanocrystals having small diameters can have properties intermediate between molecular and bulk forms of matter. For example, nanocrystals based on semiconductor materials having small diameters can exhibit quantum confinement of both the electron and hole in all three dimensions, which leads to an increase in the effective band gap of the material with decreasing crystallite size. Consequently, both the optical absorption and emission of nanocrystals shift to the blue (i.e., to higher energies) as the size of the crystallites decreases. Semiconductor nanocrystals can have a narrow fluorescence band whose emission wavelength is tunable with the size and material of the nanocrystals.

Nanocrystals consist of an inorganic nanoparticle that is surrounded by a layer of organic ligands. This organic ligand shell is critical to the nanocrystals for processing, binding to specific other moieties, and incorporation into various substrates. Fluorescent nanocrystals are most stable and robust when there is an excess amount of passivating ligands in solution. Monodentate alkyl phosphines and alkyl phosphine oxides passivate nanocrystals efficiently. Note that the term phosphine will refer to both phosphines and phosphine oxides below. Nanocrystals can be stored in their growth solution, which contains a large excess of ligands such as alkyl phosphines and alkyl phosphine oxides, for long periods without noticeable degradation. For most applications, nanocrystals must be processed outside of their growth solution and transferred into various chemical environments. However, nanocrystals often lose their high fluorescence or become irreversibly aggregated when removed from their growth solution.

SUMMARY

In general, a semiconductor nanocrystal having a polydentate ligand on the surface of the nanocrystal can be stabilized in comparison to a nanocrystal having a monodentate ligand on the surface of the nanocrystal. Monodentate ligands can readily exchange and diminish or quench emission from the nanocrystal as a result of the exchange. When nanocrystals with conventional monodentate ligands are diluted or embedded in a non-passivating environment (i.e. one where no excess ligands are present), the nanocrystals tend to lose their high luminescence and their initial chemical inertness, as manifested by, for example, an abrupt decay of luminescence, aggregation, and/or phase separation. The polydentate ligand can be a polyphosphine, a polyphosphine oxide, a polyphosphinic acid, or a polyphosphonic acid, or a salt thereof.

Advantageously, polydentate ligands, particularly oligomerized polydentate ligands such as polydentate oligomerized phosphine ligands, bind more strongly to the surface of the nanocrystal than monodentate ligands. Polydentate ligands thus stabilize the nanocrystal, which can preserve the high luminescence of as-grown nanocrystals. Polydentate phosphines can be more securely anchored onto the nanocrystal surface than bidentate thiols. In a tagging application, for example, they can ensure more secure chemical attachments of tags to their targets. In addition, because of the affinity of the polydentate ligands for the nanocrystal, minimal amounts of oligomeric phosphines can be used to passivate nanocrystals since the higher affinity and compatibility ensures a high local concentration of the ligand around the nanocrystal surface. The polydentate ligand provides a local environment that is very similar to its growth solution because the growth solution is the medium where the nanocrystal is most stable. The polydentate phosphine provides a high density phosphine ligand layer on the nanocrystal surface. Also advantageously, the outer portion of the polydentate ligand, can be chosen to be compatible with the bulk environment surrounding the nanocrystal, such as an organic solvent, aqueous media, or polymer matrix. The polydentate ligands are chemically flexible so that they can be easily functionalized to be compatible with a variety of chemical environments. For example, the polydentate ligands can be functionalized to be hydrophobic, hydrophilic, or polymerizable.

In one aspect, a semiconductor nanocrystal includes a semiconductor nanocrystal and an outer layer comprising a polydentate ligand bonded to the nanocrystal by three or more donor groups, each donor group independently selected from the group consisting of P, N, P=O, and N=O. The polydentate ligand can be a member of a distribution of oligomers. In another aspect, a semiconductor nanocrystal includes a semiconductor nanocrystal, and an outer layer including a plurality of polydentate ligands, each polydentate ligand bound to the nanocrystal by three or more donor groups, each donor group independently selected from the group consisting of P, N, P=O, and N=O, the plurality of polydentate ligands being a distribution of oligomers.

In another aspect, a semiconductor nanocrystal includes a semiconductor nanocrystal and an outer layer including a polydentate ligand bound to the nanocrystal by three or more donor groups, each donor group independently selected from the group consisting of P, N, P=O, and N=O, wherein the luminescence of the nanocrystal decreases by no more than 50% after incubating for 24 hours in fetal bovine serum maintained at 37° C.

In another aspect, a method of making a stabilized nanocrystal includes contacting a nanocrystal with a polydentate ligand having three or more donor groups, each donor group independently selected from the group consisting of P, N, P=O, and N=O, to form the stabilized nanocrystal. Stabilizing the nanocrystals can include cross-linking the polydentate ligand. The polydentate ligand can include a carboxylic acid, and cross-linking can include contacting the polydentate ligand with a diamine and a coupling agent. The polydentate ligand can include an acrylate group, and cross-linking can include contacting the polydentate ligand with a radical initiator.

In another aspect, a method of making a polydentate ligand includes contacting a monomeric, polyfunctional phosphine with a polyfunctional oligomerization reagent to form an oligomeric phosphine. The monomeric, polyfunctional phosphine can be trishydroxypropylphosphine. The polyfunctional oligomerization reagent can be a diisocyanate. The oligomeric phosphine can be contacted with an isocyanate of formula R'-L-NCO, wherein L is $C_2$-$C_{24}$ alkylene, and R' has the formula R' has the formula or R' is hydrogen, wherein $R^a$ is hydrogen or $C_1$-$C_4$ alkyl.

In yet another aspect, a method of making a nanocrystal-biomolecule conjugate includes contacting a nanocrystal including a polydentate ligand including a reactive group with a biomolecule. The biomolecule can be a polypeptide. The nanocrystal and the biomolecule can be contacted with a cross-linking agent. The reactive group can be a carboxylic acid. The biomolecule can include an amino group and the cross-linking agent can be a carbodiimide.

The first semiconductor material can be a Group II-VI compound, a Group II-V compound, a Group III-VI compound, a Group III-V compound, a Group IV-VI compound, a Group I-III-VI compound, a Group II-IV-VI compound, or a Group II-IV-V compound, such as, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. Each first semiconductor material can be overcoated with a second semiconductor material, such as ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof. The nanocrystal can be a member of a monodisperse distribution of sizes of nanocrystals. The first semiconductor material can have a smaller band gap than the second semiconductor material.

Other features, objects, and advantages of the invention will be apparent from the description and drawings, and from the claims.

DETAILED DESCRIPTION

Nanocrystal cores can be prepared by the pyrolysis of organometallic precursors in hot coordinating agents. See, for example, Murray, C. B., et al., *J. Am. Chem. Soc.* 1993, 115, 8706, and Mikulec, F., Ph.D. Thesis, MIT, Cambridge, 1999, each of which is incorporated by reference in its entirety. Growth of shell layers on the bare nanocrystal cores can be carried out by simple modifications of conventional overcoating procedures. See, for example, Peng, X., et al., *J. Am. Chem. Soc.* 1997, 119, 7019, Dabbousi, B. O., et al., *J. Phys. Chem. B* 1997, 101, 9463, and Cao, Y. W. and Banin, U. *Angew. Chem. Int. Edit.* 1999, 38, 3692, each of which is incorporated by reference in its entirety.

A coordinating agent can help control the growth of the nanocrystal. The coordinating agent is a compound having a donor lone pair that, for example, has a lone electron pair available to coordinate to a surface of the growing nanocrystal. The coordinating agent can be a solvent. A coordinating agent can stabilize the growing nanocrystal. Typical coordinating agents include alkyl phosphines, alkyl phosphine oxides, alkyl phosphonic acids, or alkyl phosphinic acids, however, other coordinating agents, such as pyridines, furans, and amines may also be suitable for the nanocrystal production. Examples of suitable coordinating agents include pyridine, tri-n-octyl phosphine (TOP) and tri-n-octyl phosphine oxide (TOPO). Technical grade TOPO can be used.

The outer surface of the nanocrystal can include a layer of compounds derived from the coordinating agent used during the growth process. The surface can be modified by repeated exposure to an excess of a competing coordinating group to form an overlayer. For example, a dispersion of nanocrystals capped with the coordinating agent used during growth can be treated with a coordinating organic compound, such as pyridine, to produce crystallites which disperse readily in pyridine, methanol, and aromatics but no longer disperse in aliphatic solvents. Such a surface exchange process can be carried out with any compound capable of coordinating to or bonding with the outer surface of the nanocrystal, including, for example, phosphines, thiols, amines and phosphates. The nanocrystal can be exposed to short chain polymers which exhibit an affinity for the surface and which terminate in a moiety having an affinity for a suspension or dispersion medium. Such affinity improves the stability of the suspension and discourages flocculation of the nanocrystal.

Monodentate alkyl phosphines and alkyl phosphine oxides passivate nanocrystals efficiently. Note that the term phosphine will refer to both phosphines and phosphine oxides below. Other conventional ligands such as thiols or phosphonic acids can be less effective than monodentate phosphines for maintaining the initial high nanocrystal luminescence over long periods. For example, the photoluminescence of nanocrystals consistently diminishes or quenches after ligand exchanges with thiols or phosphonic acid.

An excess of free monodentate phosphine ligands can maintain high nanocrystal luminescence. An excess of free phosphine ligands can favor a nanocrystal surface that is densely covered by the passivating ligands. When nanocrystals with conventional monodentate ligands are diluted or embedded in a non-passivating environment (i.e. an environment where excess ligands are not present), however, the nanocrystals can lose their high luminescence and chemical inertness. In such an environment, typical effects can include an abrupt loss of luminescence, aggregation, and/or phase separation.

In order to overcome the limitations of monodentate ligands, polydentate ligands, such as a distribution of oligomeric polydentate phosphine ligands, can be used. Polydentate ligands show a high affinity for the nanocrystal surface. In other words, a polydentate ligand can have a larger equilibrium constant for binding to a nanocrystal than a chemically similar monodentate ligand. Oligomeric phosphines have more than one binding site to the nanocrystal surface, which contributes to their high affinity for the nanocrystal surface. Oligomeric phosphines can be preferred to bidentate thiols as nanocrystal ligands because oligomeric phosphines can preserve the high luminescence of as-grown nanocrystals. Moreover, polydentate phosphines can be more securely anchored onto (i.e., have a higher affinity for) the nanocrystal surface than bidentate thiols. In a tagging application, for example, the polydentate ligand can ensure a more secure chemical attachment of a tag to its target that a monodentate ligand. Minimal amounts of oligomeric phosphines can be used to passivate nanocrystals. Unlike monodentate ligands, an excess of oligomeric phosphines is not necessary to maintain the high luminescence of nanocrystals. Oligomeric phosphines can provide the nanocrystal surface with a local environment that is very similar to its growth solution, where the nanocrystal is most stable. Polydentate phosphines can form a high-density phosphine ligand layer on the nanocrystal surface. To prevent aggregation or phase separation of nanocrystals, the outermost surface of nanocrystal must be compatible to the bulk environment. The ligands can be easily functionalized to be compatible with a variety of chemical environments. For instance, they can be functionalized to be hydrophobic, hydrophilic, or polymerizable.

The polydentate ligand can be an oligomer, or a distribution of oligomers. The polydentate ligand can have the formula:

where n is 1, 2, 3, 4 or 5, m is 1, 2, 3, 4, 5, 6, 7, 8, 9, or 10, each k is 1, 2, 3, or 4, each X is N, P, P=O or N=O, each Y is substituted or unsubstituted alkyl, substituted or unsubstituted alkoxy, substituted or unsubstituted aryl, or substituted or unsubstituted aryloxy, and L is a linking group optionally terminated by O and includes at least one carbonate, carbamate, amide, ester or ether linkage.

The polydentate ligand can be of the formula:

where n is 1, 2 or 3, m is 1, 2, 3, 4, or 5, each k is 1 or 2, each X is N, P, P=O or N=O, each Y is substituted or unsubstituted alkyl, substituted or unsubstituted alkoxy, substituted or unsubstituted aryl, or substituted or unsubstituted aryloxy, and L is a linking group optionally terminated by O and includes at least one carbonate, carbamate, amide, ester or ether linkage.

The polydentate ligand can have the formula:

where p is 1 or 2, each m is 1, 2, 3, 4, or 5, each k is 1 or 2, each j is 0 or 1, each p is 0 or 1, q is 1, 2, 3, 4, 5, 6, 7, 8, 9 or 10, each X is N, P, P=O or N=O, each Y is substituted or unsubstituted alkyl, substituted or unsubstituted alkoxy, substituted or unsubstituted aryl, or substituted or unsubstituted aryloxy, and L is a linking group optionally terminated by O and includes at least one carbonate, carbamate, amide, ester or ether linkage.

In certain circumstances, X is P or P=O, and L includes at least on carbamate linkage. In certain circumstances, each Y can be unsubstituted alkyl, each Y can include a carboxylic acid, or each Y can include an acrylate group.

The polydentate ligand can have the formula:

where n is 1, 2 or 3, m is 1, 2, 3, 4, 5, 6, 7, 8, 9, or 10, each k is 1 or 2, each x independently is 0 or 1, each of $Z^1$ and $Z^2$, independently, is an ether, amide, ester, carbamate or carbonate linkage, each $R^1$ and $R^2$, independently, is an alkylene optionally interrupted by S, O, NH, N-lower alkyl, arylene, heteroarylene, or aralkylene and optionally terminated by S, O, NH, N-lower alkyl, arylene, heteroarylene, or aralkylene, and each R is substituted or unsubstituted alkyl, substituted or unsubstituted alkoxy, or substituted or unsubstituted aryl. In certain embodiments, $Z^1$ and $Z^2$ are each a carbamate linkage. In certain circumstances, $R^1$ and $R^2$ are each an alkylene.

The polydentate ligand can have the formula:

where n is 1, 2 or 3, m is 1, 2, 3, 4, or 5, each k is 1 or 2, each x independently is 0 or 1, Z is an ether, carbamate, amide, ester or carbonate linkage, each $R^1$ and each $R^2$, independently, is an alkylene optionally interrupted by S, O, NH, N-lower alkyl, arylene, heteroarylene, or aralkylene, and optionally terminated by S, O, NH, N-lower alkyl, arylene, heteroarylene, or aralkylene, and each R is substituted or unsubstituted alkyl, or substituted or unsubstituted aryl, and each R is bonded to $R^1$ via an ether, ester, amide, carbamate or carbonate linkage.

The polydentate ligand can have the formula:

where n is 1, 2 or 3, m is 1, 2, 3, 4, or 5, each k is 1 or 2, each x independently is 0 or 1, and each R is substituted or unsubstituted alkyl, substituted or unsubstituted alkoxy, or substituted or unsubstituted aryl. R can have the formula:

The polydentate ligand can be cross-linked once bound to a nanocrystal. The cross-linked polydentate ligand can have the formula:

where each n independently is 1, 2 or 3, each m independently is 1, 2, 3, 4, or 5, each k is 1 or 2, each X is N, P, P=O or N=O, each Y is substituted or unsubstituted alkyl, substituted or unsubstituted alkoxy, substituted or unsubstituted aryl, or substituted or unsubstituted aryloxy, L is a linking group optionally terminated by O and includes at least one carbonate, carbamate, amide, ester or ether linkage, L' is a bond or a cross-linking group, and Y'-L'-Y' is derived from cross-linking of Y.

The cross-linked polydentate ligand can have the formula:

where n is 1, 2 or 3, m is 1, 2, 3, 4, or 5, each k is 1 or 2, each x is 0 or 1, and each R is substituted or unsubstituted alkyl, or substituted or unsubstituted aryl, L' is a bond or a cross-linking group, and R'-L'-R' is derived from cross-linking of R. When each R includes a carboxylic acid, the polydentate ligand can be cross-linked with, for example, a diamine, and R'-L'-R' can include the fragment:

where A is alkylene or arylene. When each R includes an acrylate group, the polydentate ligand can be cross-linked by radical polymerization of the acrylate groups, and R'-L'-R' can include the fragment:

where A' is H or $C_1$-$C_4$ alkyl.

Figure 1:
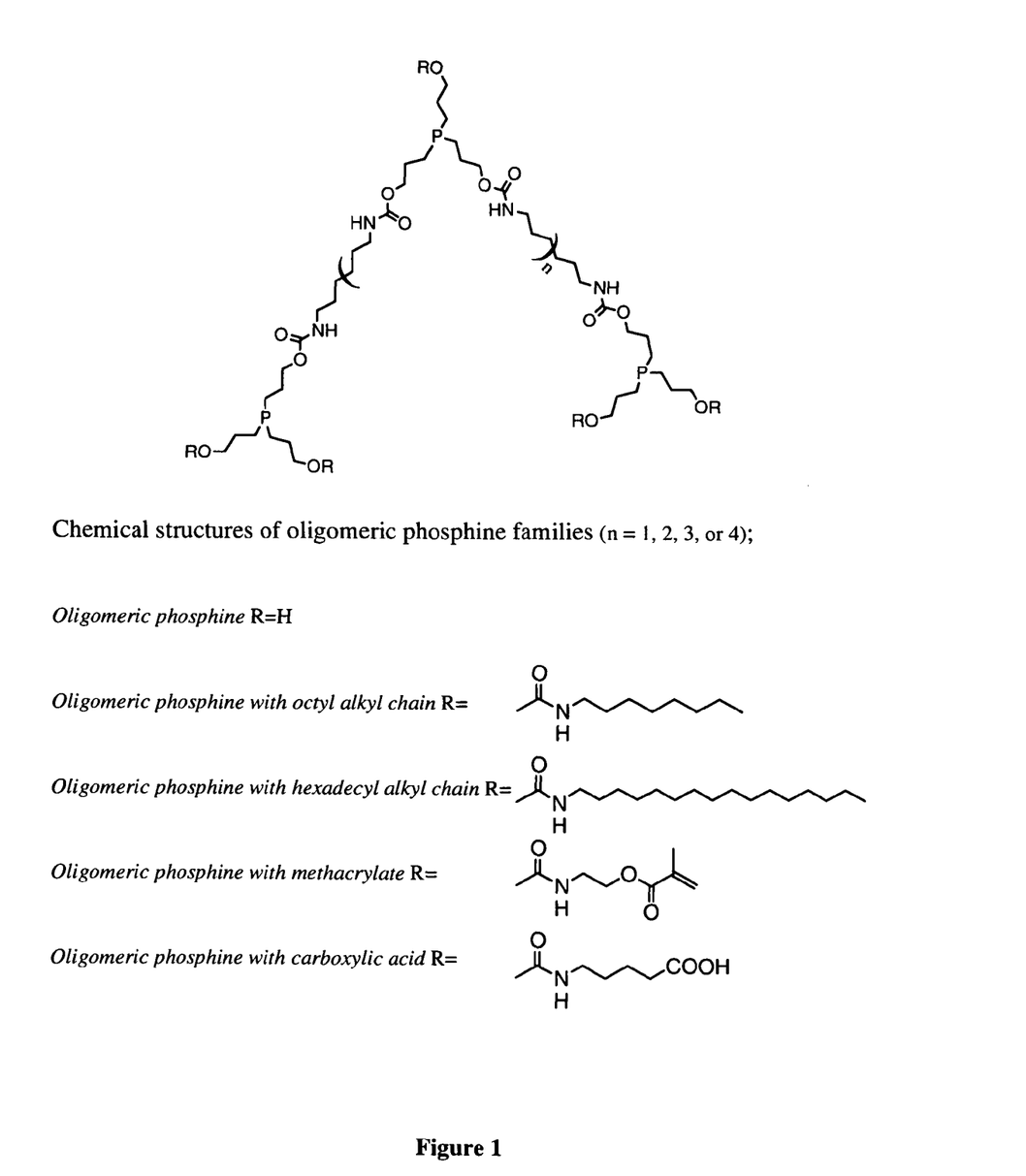
FIG. 1 is a diagram depicting representative chemical structures of oligomeric phosphines.

FIG. 1 shows chemical structures of representative oligomeric phosphines with functionalized branches. The exemplary functional groups shown are alkyl, methacrylate, and carboxylic acid. Many other functional groups can be introduced with minor modifications to the synthesis. This flexibility can allow homogeneous incorporation of nanocrystals in any desired medium.

The oligomeric ligands can create a trilayer around the nanocrystal: a phosphine layer, a hydrophobic linking layer, and a functionalized layer. The phosphine layer can passivate the nanocrystal surface, the hydrophobic layer can protect it, while the functionalized layer can deliver desirable chemical properties including solubility, miscibility, the ability to copolymerize with other matrices, further cross-linking on the surface of the nanocrystals, and other derivatizations such as conjugation to biomolecules.

The synthesis of oligomeric phosphines (such as those shown in FIG. 1) and methods for ligand exchange on nanocrystal surfaces are described below. The synthesis is flexible and can be easily modified. In general, a monomeric phosphine is oligomerized, and the resulting oligomeric phosphine is functionalized. A specific example is shown in Scheme 1, which can be easily generalized and modified to synthesize the polydentate ligands described here. As shown in Scheme 1, a monomeric phosphine such as trishydroxypropylphosphine (THPP) can be oligomerized by reaction with a multifunctional linker such as diisocyanatohexane (DIH). Though Scheme 1 shows a linear oligomer, branched oligomers are possible. The linker can be a bifunctional, trifunctional or higher functional linker. The distribution of oligomers can be controlled by adjusting the stoichiometry of the monomeric unit and linker. In certain circumstances, the distribution of oligomers includes primarily oligomers with n=1, 2, 3, or 4 according to Scheme 1. Many other linkers can also be used. Various alkyldiisocyanates with different length alkyl chains and aryldiisocyanates are commercially available (for example, from Sigma-Aldrich) and can act as varying length spacers between phosphine groups within the oligomers.

The oligomeric phosphine can be functionalized, for example by reaction with a second isocyanate including a group that bestows a desired property on the functionalized oligomeric phosphine. The second isocyanate is represented in Scheme 1 as R—NCO. For example, if the desired property is hydrophobicity, the second isocyanate can include a hydrophobic group such as an alkyl chain, as in octyl isocyanate or hexadecyl isocyanate. Other examples of properties that can be introduced include hydrophilicity (e.g. from a hydrophilic group such as a carboxylic acid) and ability to polymerize (e.g. from a polymerizable group such as an acrylate or methacrylate). See FIG. 1. In some circumstances, the ligand can be exposed to oxygen (for example, air) to oxidize the donor atoms (i.e. P or N).

Chemical functionality can be introduced to the small oligomeric phosphine by further reactions with any molecule or a combination of molecules. The functionality can be introduced, for example, by reaction of an oligomeric phosphine having unreacted hydroxyl groups with a molecule having a desired functional group and an isocyanate group. See Scheme 1. For example, octylisocyanate or hexadecylisocyanate can be used to introduce a hydrophobic alkyl chain, and a polymerizable methacrylate group can be introduced by reaction with 2-isocyanatoethylmethacrylate. In some cases, conventional protection and deprotection procedures on the desired functional group may be necessary to facilitate synthesis. An oligomeric phosphine bearing carboxylic acid groups (FIG. 1) can be prepared by hydrolysis of an ester derivatized oligomeric phosphine. The ester derivatized oligomeric phosphine can prepared from the reaction between the oligomeric phosphine and methyl-5-isocyanatopentanoate. Advantageously, the ester can be selectively hydrolyzed under basic hydrolysis conditions while retaining the carbamate linkages.

Carbamate bond formation between a monomeric phosphine, such as THPP, and a diisocyanate such as DIH can be advantageous as an oligomerization reaction. Advantages of this oligomerization reaction include a reaction to completeness under mild conditions at room temperature. The monomeric phosphine, in addition to serving as a reactant, can catalyze the carbamate bond formation reaction. Tin compounds such as dibutyltin dilaurate can be added to further catalyze the reaction. See, for example, Ulrich, H., *Chemistry and technology of isocyanates* 1996, Chichester, N.Y., J. Wiley & Sons, which is incorporated by reference in its entirety. Another advantage is the small extent of side reactions, such that purification can be unnecessary. An additional advantage is that the carbamate bond can be stable enough for most purposes such as fluorescence in situ hybridization procedures. See, for example, Pathak, S., et al., 2001 *J. Am. Chem. Soc.* 123, 4103, and Palm, V. A., *Tables of rate and equilibrium constants of heterolytic organic reactions* V.1 1975 Laboratory of chemical kinetics and catalysis at Tartu State University, Moscow, each of which is incorporated by reference in its entirety.

Figure 2:
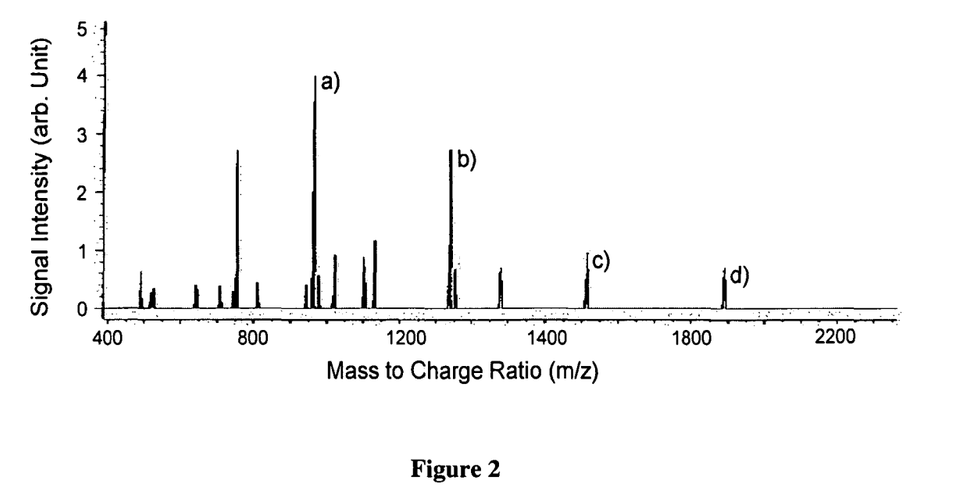
FIG. 2 is a graph depicting the mass spectrum of oligomeric phosphine.

In one example of a polydentate ligand, FIG. 2 shows a mass spectrum of an unfunctionalized oligomeric phosphine, and reveals a narrow distribution of oligomers. Labels a), b), c) and d) indicate peaks that correspond to the oligomeric phosphine depicted in Scheme 1, with n=1, n=2, n=3, and n=4, respectively. The mass spectrum was recorded with a Bruker Daltonics APEX3 with an electrospray ionization source. Peaks from multiple charges were deconvoluted to singly charged mass numbers to demonstrate the distribution of oligomers.

SCHEME 1

Ligand exchanges (e.g. substitution of an oligomeric phosphine for a monodentate phosphine) can be carried out by one-phase or two-phase methods. Prior to ligand exchange, nanocrystals can be precipitated from their growth solutions by addition of methanol. The supernatant solution, which includes excess coordinating agent (e.g., trioctylphosphine), can be discarded. The precipitated nanocrystals can be redispersed in hexanes. Precipitation and redispersion can be repeated until essentially all the excess coordinating agent has been separated from the nanocrystals. A one-phase process can be used when both the nanocrystals and the ligands to be introduced are soluble in the same solvent. A solution with an excess of new ligands can be mixed with the nanocrystals. The mixture can be stirred at an elevated temperature until ligand exchange is complete. The one-phase method can be used, for example, to exchange octyl-modified oligomeric phosphines or methacrylate-modified oligomeric phosphines, which are both soluble in solvents that are compatible with the nanocrystals, such as hexanes. A two-phase ligand exchange process can be preferable when the nanocrystals and the new ligands do not have a common solvent. Nanocrystals can dissolved in an organic solvent such as dichloromethane, and the new ligand can be dissolved in an aqueous solution. The nanocrystals can be transferred from the organic phase to the aqueous phase by, for example, sonication. The transfer can be monitored through absorption and emission spectroscopy. A carboxylic acid-modified oligomeric phosphine can be introduced to nanocrystals via this method. A similar two-phase ligand exchange process has been reported earlier. See, for example, Wang, Y. A., et al., 2002 *J. Am. Chem. Soc* 124, 2293, incorporated by reference in its entirety.

Figure 3:
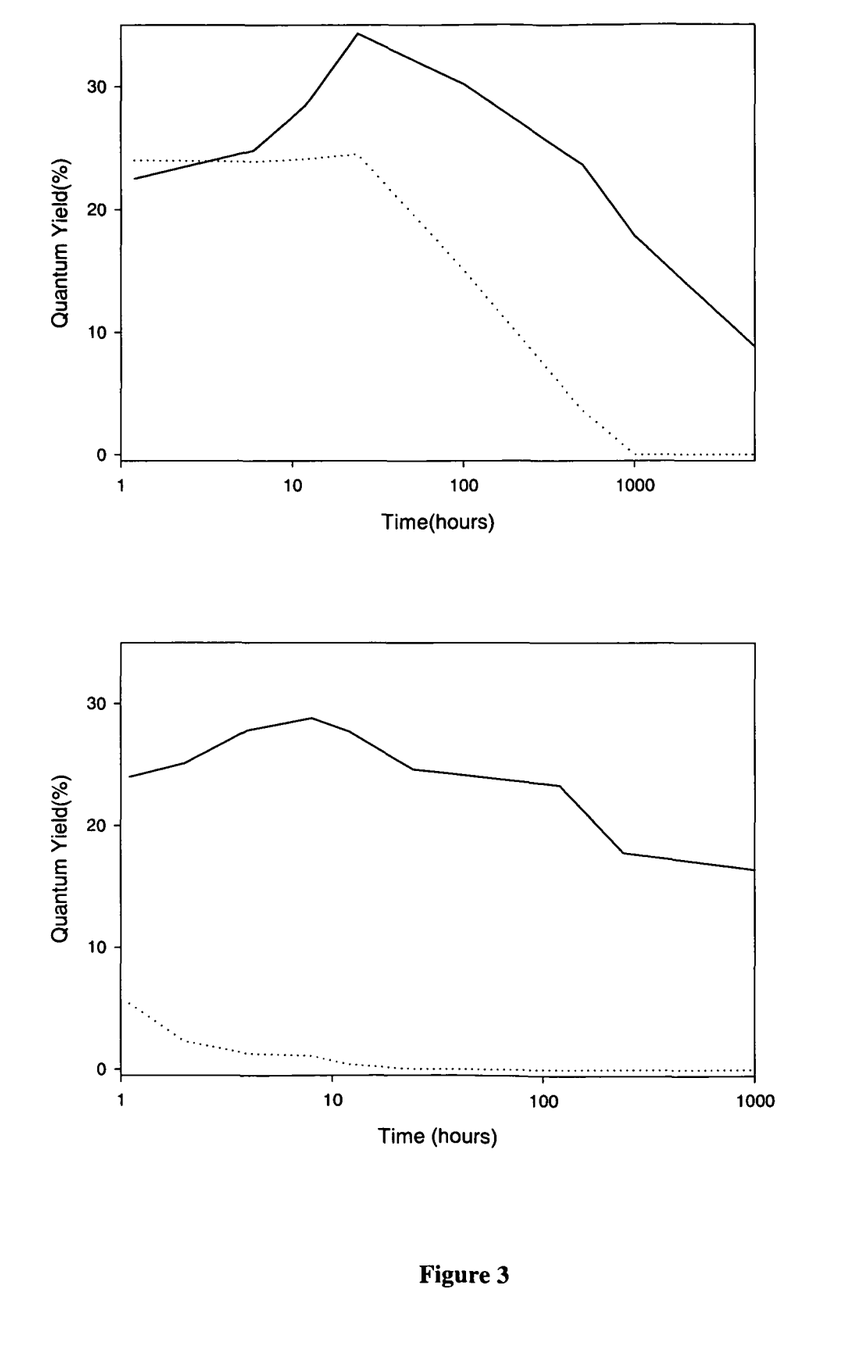
FIG. 3 is a set of graphs depicting quantum yield changes over time of identical CdSe/ZnS nanocrystals passivated by different ligands.

FIG. 3 shows a comparison of nanocrystal stability in the presence of oligomeric phosphine ligands or monomeric ligands. The comparison was made in organic solvent and in aqueous solution. Equimolar binding sites (i.e. phosphine or thiol moieties) were used, with only a slight excess of ligand present relative to the concentration of nanocrystal. This ensures that there are very small amounts of extra free ligands in the solution. Therefore, the stabilities of photoluminescence can be validated as a method to measure the different binding affinities and passivating powers of the ligands on nanocrystal surface. The top panel shows that nanocrystals dispersed in THF, passivated by oligomeric phosphine with hexadecyl alkyl chain (solid line) are more stable than those passivated by trioctylphosphine (dotted line). The bottom panel shows that, in aqueous 0.1 M potassium hydroxide, nanocrystals passivated by oligomeric phosphine with carboxylic acid (solid line) are greatly stabilized compared to nanocrystals passivated by mercaptoundecanoic acid (dotted line).

In certain circumstances, a functionalized oligomeric phosphine can be cross-linked once bound to the nanocrystal. Such cross-linking can further increase the stability of the nanocrystals. Cross-linking can be accomplished by, for example, addition of a diamine such as 2,6-diaminopimelic acid a carbodiimide dehydrating agent to carboxylic acid-functionalized oligomeric phosphine. Cross-linking can be carried out while the ligand is bound to a nanocrystal. Another example of cross-linking is the radical polymerization of the methacrylate groups of a methacrylate-modified oligomeric phosphine.

Nanocrystals with oligomeric phosphine ligands can be conjugated to biomolecules. For example, nanocrystals having carboxylic acid-modified oligomeric phosphine ligands can be coupled to biomolecules containing amino groups. The coupling can be facilitated by a carbodiimide dehydrating agent, such as EDC (1-ethyl-3-(3-dimethylaminopropyl)-carbodiimide hydrochloride). The general coupling reaction is described, for example, in Hermanson, G. T. *Bioconjugate Techniques* 1996 Academic Press, which is incorporated by reference in its entirety. Electrostatic interactions can be also used as thiol-based ligands with carboxylic acid. See, for example, Mattoussi, H., et al., *J. Am. Chem. Soc.* 2000, 122, 12142, and Goldman, E. R., et al., 2002 *J. Am. Chem. Soc.* 124, 6378, each of which is incorporated by reference in its entirety. Additional cross-linking agents that can couple nanocrystals with oligomeric phosphine ligands to biomolecules include carbonyldiimidazole and epichlorohydrin. See, for example, Pathak S., et al., 2001 *J. Am. Chem. Soc* 123, 4103, and Hermanson, G. T. *Bioconjugate Techniques* 1996 Academic Press, each of which is incorporated by reference in its entirety.

The nanocrystal can be a member of a population of nanocrystals having a narrow size distribution. The nanocrystal can be a sphere, rod, disk, or other shape. The nanocrystal can include a core of a semiconductor material. The nanocrystal can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof.

The semiconductor forming the core of the nanocrystal can include Group II-VI compounds, Group II-V compounds, Group III-VI compounds, Group III-V compounds, Group IV-VI compounds, Group compounds, Group II-IV-VI compounds, and Group II-IV-V compounds, for example, ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

The core can have an overcoating on a surface of the core. The overcoating can be a semiconductor material having a composition different from the composition of the core. The overcoat of a semiconductor material on a surface of the nanocrystal can include a Group II-VI compounds, Group II-V compounds, Group III-VI compounds, Group III-V compounds, Group IV-VI compounds, Group I-III-VI compounds, Group II-IV-VI compounds, and Group II-IV-V compounds, for example, ZnS, ZnSe, ZnTe, CdS, CdSe, CdTe, HgS, HgSe, HgTe, MN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof. The overcoating material can have a band gap greater than the band gap of the core material. Alternatively, the overcoating material can have a band (i.e. the valence band or the conduction band) intermediate in energy to the valence and conduction bands of the core material. See for example, U.S. patent application No. 10/638,546, titled, "Semiconductor Nanocrystal Heterostructures", filed Aug. 12, 2003, now U.S. Pat. No. 7,390,568 which is incorporated by reference in its entirety.

The emission from the nanocrystal can be a narrow Gaussian emission band that can be tuned through the complete wavelength range of the ultraviolet, visible, or infrared regions of the spectrum by varying the size of the nanocrystal, the composition of the nanocrystal, or both. For example, CdSe can be tuned in the visible region and InAs can be tuned in the infrared region.

The population of nanocrystals can have a narrow size distribution. The population can be monodisperse and can exhibit less than a 15% rms deviation in diameter of the nanocrystals, preferably less than 10%, more preferably less than 5%. Spectral emissions in a narrow range of between 10 and 100 nm full width at half max (FWHM) can be observed. Semiconductor nanocrystals can have emission quantum efficiencies of greater than 2%, 5%, 10%, 20%, 40%, 60%, 70%, or 80%.

Methods of preparing semiconductor nanocrystals include pyrolysis of organometallic reagents, such as dimethyl cadmium, injected into a hot, coordinating agent. This permits discrete nucleation and results in the controlled growth of macroscopic quantities of nanocrystals. Preparation and manipulation of nanocrystals are described, for example, in U.S. Pat. No. 6,322,901, incorporated herein by reference in its entirety. The method of manufacturing a nanocrystal is a colloidal growth process and can produce a monodisperse particle population. Colloidal growth occurs by rapidly injecting an M donor and an X donor into a hot coordinating agent. The injection produces a nucleus that can be grown in a controlled manner to form a nanocrystal. The reaction mixture can be gently heated to grow and anneal the nanocrystal. Both the average size and the size distribution of the nanocrystals in a sample are dependent on the growth temperature. The growth temperature necessary to maintain steady growth increases with increasing average crystal size. The nanocrystal is a member of a population of nanocrystals. As a result of the discrete nucleation and controlled growth, the population of nanocrystals obtained has a narrow, monodisperse distribution of diameters. The monodisperse distribution of diameters can also be referred to as a size. The process of controlled growth and annealing of the nanocrystals in the coordinating agent that follows nucleation can also result in uniform surface derivatization and regular core structures. As the size distribution sharpens, the temperature can be raised to maintain steady growth. By adding more M donor or X donor, the growth period can be shortened.

An overcoating process is described, for example, in U.S. Pat. No. 6,322,901, incorporated herein by reference in its entirety. By adjusting the temperature of the reaction mixture during overcoating and monitoring the absorption spectrum of the core, over coated materials having high emission quantum efficiencies and narrow size distributions can be obtained.

The M donor can be an inorganic compound, an organometallic compound, or elemental metal. The inorganic compound M-containing salt can be a metal halide, metal carboxylate, metal carbonate, metal hydroxide, or metal diketonate, such as a metal acetylacetonate. See, for example, U.S. Pat. No. 6,576,291, which is incorporated by reference in its entirety. M is cadmium, zinc, magnesium, mercury, aluminum, gallium, indium or thallium. The X donor is a compound capable of reacting with the M donor to form a material with the general formula MX. Typically, the X donor is a chalcogenide donor or a pnictide donor, such as a phosphine chalcogenide, a bis(silyl)chalcogenide, dioxygen, an ammonium salt, or a tris(silyl)pnictide. Suitable X donors include dioxygen, bis(trimethylsilyl)selenide ($(TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl)telluride ($(TMS)_2Te$), bis(trimethylsilyl)sulfide ($(TMS)_2S$), a trialkyl phosphine sulfide such as (tri-n-octylphosphine) sulfide (TOPS), an ammonium salt such as an ammonium halide (e.g., $NH_4Cl$), tris(trimethylsilyl)phosphide ($(TMS)_3P$), tris(trimethylsilyl)arsenide ($(TMS)_3As$), or tris(trimethylsilyl)antimonide ($(TMS)_3Sb$). In certain embodiments, the M donor and the X donor can be moieties within the same molecule.

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. By stopping growth at a particular nanocrystal average diameter, a population having an average nanocrystal diameter of less than 150 Å can be obtained. A population of nanocrystals can have an average diameter of 15 Å to 125 Å.

The particle size distribution can be further refined by size selective precipitation with a poor solvent for the nanocrystals, such as methanol/butanol as described in U.S. Pat. No. 6,322,901, incorporated herein by reference in its entirety. For example, nanocrystals can be dispersed in a solution of 10% butanol in hexane. Methanol can be added dropwise to this stirring solution until opalescence persists. Separation of supernatant and flocculate by centrifugation produces a precipitate enriched with the largest crystallites in the sample. This procedure can be repeated until no further sharpening of the optical absorption spectrum is noted. Size-selective precipitation can be carried out in a variety of solvent/nonsolvent pairs, including pyridine/hexane and chloroform/methanol. The size-selected nanocrystal population can have no more than a 15% rms deviation from mean diameter, preferably 10% rms deviation or less, and more preferably 5% rms deviation or less.

Transmission electron microscopy (TEM) can provide information about the size, shape, and distribution of the nanocrystal population. Powder X-ray diffraction (XRD) patterns can provided the most complete information regarding the type and quality of the crystal structure of the nanocrystals. Estimates of size are also possible since particle diameter is inversely related, via the X-ray coherence length, to the peak width. For example, the diameter of the nanocrystal can be measured directly by transmission electron microscopy or estimated from X-ray diffraction data using, for example, the Scherrer equation. It also can be estimated from the UV/Vis absorption spectrum.

EXAMPLES

All the procedures described here are carried out under an inert atmosphere unless specified otherwise. All commercial chemicals are used directly without any purification.

Oligomeric phosphines were synthesized by polymerizing an alkyl phosphine, which was further functionalized in a subsequent reaction. Oligomeric phosphines refer to a distribution of oligomerized phosphines. The distribution of oligomerized phosphines includes primarily of oligomers with n=1, 2, 3, and 4 (see Scheme 1).

Oligomeric phosphines were synthesized as follows. Trishydroxypropylphosphine (8.00 g) (THPP, Strem, 90%) of was dissolved in 20.0 g of dimethylformamide (DMF, Aldrich, 99.8%). Diisocyanatohexane (4.54 g) (DIH, Aldrich, 98%) was added dropwise while the solution was vigorously stirred. After the addition was complete, the solution was stirred overnight. The solvent was removed at a reduced pressure and the mixture was characterized by mass spectroscopy. ESI-MS (m/z): exp. 961.6 ($M+H^+$), calc. 961.6 for n=1 in Scheme 1, exp. 1337.9 ($M+H^+$), calc. 1337.8 for n=2 in Scheme 1, exp. 1713.9 ($M+H^+$), calc. 1714.0 for n=3 in Scheme 1, exp. 2090.3 ($M+H^+$), calc. 2090.2 for n=4 in Scheme 1. See FIG. 2.

Oligomeric phosphines were functionalized with octyl alkyl chains to form octyl-modified oligomeric phosphines. The octyl-modified oligomeric phosphines are compatible with hydrophobic environments, and after exchange with the existing surface capping groups, can render the nanocrystals compatible also with many hydrophobic environments.

The octyl-modified oligomeric phosphines were synthesized as follows. Oligomeric phosphines (2.86 g, prepared as above) were dissolved in 3.0 mL of DMF. Octylisocyanate (2.31 g) (Aldrich, 97%) was added dropwise. After the addition was complete, the solution was stirred overnight. The solvent was removed at a reduced pressure. The mixture was characterized by mass spectroscopy. ESI-MS (m/z): exp. 1737.2 ($M+H^+$), calc. 1737.2 for n=1 in Scheme 1, exp. 2268.6 ($M+H^+$), calc. 2268.6 for n=2 in Scheme 1.

The oligomeric phosphines were exchanged with the nanocrystal surface capping groups as follows. CdSe/ZnS nanocrystal powder free of excess trioctylphosphine oxide was obtained by nonsolvent-precipitation methods from 0.1 mL growth solution. Octyl-modified oligomeric phosphines (0.2 mL) in DMF solution (64% wt/wt) and 3.0 mL of THF were added to the nanocrystal powder and stirred vigorously at 60° C. for overnight. The resultant nanocrystals were now capped with the octyl-modified oligomeric phosphine ligands. During the steps described above, an excess amount of new ligands were used to complete the ligand-exchange. The excess ligands were removed by precipitation followed by ultra-centrifugation. The precipitation can be induced by the addition of methanol to the solution.

Hexadecyl-modified oligomeric phosphines were also prepared that were compatible with many hydrophobic environments, and after exchange with surface capping groups, rendered the nanocrystals compatible with many hydrophobic environments. These ligands were prepared in the same manner as the small oligomeric phosphines with octyl alkyl chains except 3.98 g of hexadecylisocyanate (Aldrich, 97%) were used in place of 2.31 g octylisocyanate.

Methacrylate-modified oligomeric phosphines can allow nanocrystals to be incorporated into polymer media by co-polymerization, which can reduce or prevent the occurrence of phase separation of nanocrystals. The methacrylate-modified oligomeric phosphines were prepared as follows. Oligomeric phosphines (3.0 g) of in DMF solution (40% wt/wt) were diluted by 6.0 mL of DMF. The solution was stirred vigorously in an ice bath while 0.97 g of 2-isocyanatoethyl-methacrylate (Aldrich, 98%) was slowly added for 4 hours. After the addition, the solution was stirred in the ice bath overnight. The solvent was removed at a reduced pressure.

The exchange of capping groups was carried out as follows. CdSe/ZnS nanocrystal powder free of excess trioctylphosphine oxide was obtained by standard nonsolvent-precipitation methods from 0.1 mL growth solution. Oligomeric phosphines with methacrylate in DMF solution (40% wt/wt, 0.3 mL) was added to the nanocrystals and stirred vigorously overnight. The nanocrystals were now capped with the new ligand and possess the methacrylate functionality for further chemistry. During the steps above, an excess amount of new ligands were used to complete the ligand-exchange. The excess ligands were removed by precipitation followed by ultra-centrifugation. The precipitation can be induced by an addition of acetonitrile.

Oligomeric phosphines with carboxylic acid are compatible with aqueous environments, including biological environments. The carboxylic acid is available for further standard coupling chemistries. The small oligomeric phosphines with carboxylic acid was prepared as follows. Oligomeric phosphines (0.16 g) were dissolved in 2.0 mL of DMF. Methyl-5-isocyanatopentanoate (0.26 g) (synthesis below) was added dropwise. After the addition was complete, the solution was stirred overnight. The solvent was removed at a reduced pressure. Potassium hydroxide (Mallinckrodt, 88%, 0.5 g), 2.0 mL of tetrahydrofuran (Aldrich, 99.9%) and 2.0 mL of distilled water were added and stirred vigorously at 60° C. for 1 day. The solvent was removed at a reduced pressure.

Methyl-5-isocyanatopentanoate was synthesized by combining 1.0 g of methyladipoylchloride (Lancaster, 96%), 0.4 g sodium azide (Aldrich, 99%) and 4.0 mL of benzene (Aldrich, 99.8%) were mixed and stirred for 1 day. The mixture was passed through a filter paper, and vacuum distilled.

The oligomeric phosphines with carboxylic acid were exchanged with surface capping groups as follows. Out of 1.0 mL growth solution, a CdSe/ZnS nanocrystal powder, free of excess trioctylphosphine oxide, was obtained by nonsolvent-precipitation methods and dissolved in 3.0 mL of dichloromethane (Aldrich, 99.6%). 10 mL of 0.2 M oligomeric phosphines with carboxylic acid/KOH aqueous solution (described above) was added to the powder. The mixture was sonicated overnight. The emulsified solution was separated into two different layers by centrifugation. The aqueous layer was obtained by decanting after verifying that the nanocrystals were completely transferred in. These nanocrystals were derivatized with a polyphosphine carboxylic acid. During the steps above, an excess amount of new ligands was used to complete the ligand-exchange. The excess ligands can be removed by dialysis, for example by repeated dilution and filtration using a membrane centrifugal dialysis kit of nominal molecular cut-off of 50,000 daltons.

CdSe/ZnS(core/shell) nanocrystals were ligand-exchanged with oligomeric phosphine with carboxylic acid as follows. Excess ligands were rigorously removed by repeated dialysis. A 0.1 M MES was introduced, and the number of semiconductor nanocrystal particles in the solution was determined by measuring the optical absorption. See Leatherdale, C. A.; Woo, W. K.; Mikulec, F. V.; Bawendi, M. G. *Journal of Physical Chemistry B* 2002, 106, 7619, which is incorporated by reference in its entirety. The carbodiimide cross-linking agent EDC (1-ethyl-3-(3-dimethylaminopropyl)carbodiimide hydrochloride, Pierce, 25,000 equivalents) and 125,000 equivalents of N-hydroxysulfosuccinimide (Pierce) per nanocrystal were added to the nanocrystal solution. The solution was incubated for 15 minutes, and excess reagents were removed by dialysis in 0.1 M MES buffer. A PBS solution containing 5,000 equivalents of 2,6-diaminopimelic acid (Aldrich, 98%) was mixed with the MES solution. The final pH was around 7.0 after mixing. The reaction solution was incubated for 4 hours and the ligand-exchange and cross-linked nanocrystals were purified by repeated dialysis.

The stability of cross-linked nanocrystals bound by oligomeric phosphine with carboxylic acid was compared to non-cross-linked nanocrystals by monitoring luminescence change over 100% fetal bovine serum at 37° C. over 24 hours. The cross-linked nanocrystals experienced less than 20% loss of luminescence, whereas the luminescence of noncross-linked nanocrystals decreased by more than 50%.

Streptavidin conjugation to CdSe/ZnS(core/shell) nanocrystals bound to oligomeric phosphine with carboxylic acid was carried out by a procedure similar to that described above for cross-linking. 100 equivalents of streptavidin (Pierce) were used instead of 2,6-diaminopimelic acid. Streptavidin conjugation can also be achieved with nanocrystals previously cross-linked by 2,6-diaminopimelic acid. Fluorescence micrographs revealed that streptavidin conjugated nanocrystals bound specifically to biotin-agarose beads, whereas nanocrystals not conjugated to streptavidin did not.

Oligomeric phosphines with methacrylate can enable homogeneous incorporation (i.e., co-polymerization) of nanocrystals into many polymer matrices without the need for additional free ligands such as TOP in the matrix. The polymerizable ligands can become incorporated into host polymers and offer synthetic routes to micron and sub-micron sized polymer-nanocrystal composites. For example, fluorescent polymer sticks incorporating semiconductor nanocrystals were prepared as follows: CdSe/ZnS(core/shell) nanocrystals were ligand-exchanged with oligomeric phosphine with methacrylate and mixed with hydroxypropyl methacrylate (Aldrich, 97%), ethyleneglycol dimethacrylate (Aldrich, 98%), and a small amount (<1% wt/wt) of 2,2'-azobisisobutyronitrile (Aldrich, 98%). The solution was transferred to a glass tube and partially immersed in an oil bath at 70° C. until the polymerization was complete, ~3 hours.

Other embodiments are within the scope of the following claims.

What is claimed is:

1. A semiconductor nanocrystal composition comprising:
a semiconductor nanocrystal; and
an outer layer including a functionalized polydentate ligand bound to the nanocrystal by three or more donor groups, each donor group independently selected from the group consisting of P, N, P=O, and N=O, wherein the polydentate ligand includes a phosphine, and wherein the outer portion of the functionalized polydentate ligand is compatible with a hydrophobic environment.

2. The nanocrystal composition of claim 1, wherein the semiconductor nanocrystal includes a core of a first semiconductor material.

3. The nanocrystal composition of claim 2, wherein the first semiconductor material is a Group II-VI compound, a Group II-V compound, a Group III-VI compound, a Group III-V compound, a Group IV-VI compound, a Group I-III-VI compound, a Group II-IV-VI compound, or a Group II-IV-V compound.

4. The nanocrystal composition of claim 2, wherein the first semiconductor material is ZnS, ZnSe, ZnTe, CdS, CdSe, CdTe, HgS, HgSe, HgTe, AlN, AlP, AlAs, AlSb, GaN, GaP, GaAs, GaSb, GaSe, InN, InP, InAs, InSb, TlN, TlP, TlAs, TlSb, PbS, PbSe, PbTe, or mixtures thereof.

5. The nanocrystal composition of claim 2, wherein the semiconductor nanocrystal includes a second semiconductor material overcoated on the first semiconductor material.

6. The nanocrystal composition of claim 5, wherein the first semiconductor material has a first band gap, and the second semiconductor material has a second band gap that is larger than the first band gap.

7. The nanocrystal composition of claim 5, wherein the second semiconductor material is a Group II-VI compound, a Group II-V compound, a Group III-VI compound, a Group III-V compound, a Group IV-VI compound, a Group I-III-VI compound, a Group II-IV-VI compound, or a Group II-IV-V compound.

8. The nanocrystal composition of claim 5, wherein the second semiconductor material is ZnO, ZnS, ZnSe, ZnTe, CdO, CdS, CdSe, CdTe, MgO, MgS, MgSe, MgTe, HgO, HgS, HgSe, HgTe, AlN, AlP, AlAs, AlSb, GaN, GaP, GaAs, GaSb, InN, InP, InAs, InSb, TlN, TlP, TlAs, TlSb, TlSb, PbS, PbSe, PbTe, or mixtures thereof.

9. A semiconductor nanocrystal in accordance with claim 1 wherein the outer layer comprises a plurality of polydentate ligands, wherein the plurality of polydentate ligands comprises a distribution of oligomers.

10. A method of making a stabilized nanocrystal comprising contacting a nanocrystal with a functionalized polydentate ligand having three or more donor groups, each donor group independently selected from the group consisting of P, N, P=O, and N=O, to form the stabilized nanocrystal, wherein the polydentate ligand includes a phosphine, and wherein the outer portion of the functionalized polydentate ligand is compatible with a hydrophobic environment.

11. The method of claim 10, wherein the polydentate ligand is a member of a distribution of oligomers.

12. The method of claim 10, further comprising cross-linking the polydentate ligand after contacting.

13. The method of claim 12, wherein the polydentate ligand includes a carboxylic acid group.

14. The method of claim 13, wherein cross-linking includes contacting the polydentate ligand with a diamine and a coupling agent.

15. The method of claim 12, wherein the polydentate ligand includes an acrylate group.

16. The method of claim 15, wherein cross-linking includes contacting the polydentate ligand with a radical initiator.

17. A semiconductor nanocrystal including an outer layer comprising a functionalized polydentate ligand bonded to the nanocrystal by three or more donor groups, each donor group comprising P or P=O, wherein the polydentate ligand includes a phosphine, and wherein the outer portion of the functionalized polydentate ligand is compatible with a hydrophobic environment.

18. A semiconductor nanocrystal in accordance with claim 17, wherein the polydentate ligand comprises a polyphosphine.

19. A semiconductor nanocrystal in accordance with claim 17, wherein the polydentate ligand comprises a polyphosphine oxide.

20. A semiconductor nanocrystal in accordance with claim 17, wherein the polydentate ligand comprises a polyphosphinic acid or a salt of a polyphosphinic acid.

21. A semiconductor nanocrystal in accordance with claim 17, wherein the polydentate ligand comprises a polyphosphinic acid or a salt of a polyphosphonic acid.

* * * * *